United States Patent
Jadhav et al.

(10) Patent No.: US 11,248,005 B2
(45) Date of Patent: Feb. 15, 2022

(54) PROCESS FOR PREPARATION OF INTERMEDIATES USED FOR THE SYNTHESIS OF HIV INTEGRASE INHIBITOR

(71) Applicant: Lupin Limited, Mumbai (IN)

(72) Inventors: Harishchandra Sambhaji Jadhav, Pune (IN); Dhananjai Shrivastava, Pune (IN); Umesh Parasharam Aher, Pune (IN); Sharad Chandrabhan Deokar, Pune (IN); Deepak Babasaheb Nale, Pune (IN); Suryakant Tukaram Honrao, Pune (IN); Girij Pal Singh, Pune (IN)

(73) Assignee: Lupin Limited, Mumbai (IN)

( * ) Notice: Subject to any disclaimer, the term of this patent is extended or adjusted under 35 U.S.C. 154(b) by 0 days.

(21) Appl. No.: 16/922,260

(22) Filed: Jul. 7, 2020

(65) Prior Publication Data

US 2021/0009606 A1 Jan. 14, 2021

(30) Foreign Application Priority Data

Jul. 8, 2019 (IN) .............................. 201921027344

(51) Int. Cl.
*C07D 498/14* (2006.01)
*C07D 498/18* (2006.01)

(52) U.S. Cl.
CPC .................................. *C07D 498/14* (2013.01)

(58) Field of Classification Search
CPC ............................ C07D 498/14; C07D 498/18
See application file for complete search history.

(56) References Cited

FOREIGN PATENT DOCUMENTS

| | | |
|---|---|---|
| WO | 2006116764 A1 | 11/2006 |
| WO | 2010068262 A1 | 6/2010 |
| WO | 2011119566 A1 | 9/2011 |
| WO | 2011129095 A1 | 10/2011 |
| WO | 2012018065 A1 | 2/2012 |
| WO | 2014100323 A1 | 6/2014 |
| WO | 2014128545 A2 | 8/2014 |
| WO | 2015006731 A1 | 1/2015 |
| WO | 2015019310 A1 | 2/2015 |
| WO | 2015110897 A2 | 7/2015 |
| WO | 2015111080 A2 | 7/2015 |
| WO | 2015195656 A2 | 12/2015 |
| WO | 2016092527 A1 | 6/2016 |
| WO | 2016113372 A1 | 7/2016 |
| WO | 2018229798 A1 | 12/2018 |
| WO | 2010068253 A1 | 6/2020 |

*Primary Examiner* — Brenda L Coleman
(74) *Attorney, Agent, or Firm* — The Webb Law Firm

(57) ABSTRACT

Provided herein is a process for the intermediates used for preparation of HIV Integrase Inhibitor such as Bictegravir, Dolutegravir, Cabotegravir or their pharmaceutically acceptable salts.

20 Claims, No Drawings

PROCESS FOR PREPARATION OF INTERMEDIATES USED FOR THE SYNTHESIS OF HIV INTEGRASE INHIBITOR

CROSS-REFERENCE TO RELATED APPLICATION

This application claims priority to Indian Patent Application No. 201921027344 filed Jul. 8, 2019, the disclosure of which is hereby incorporated by reference in its entirety.

BACKGROUND OF THE INVENTION

Field of the Invention

The present invention provides a process for the preparation of intermediates and their use in the preparation of HIV Integrase Inhibitor such as Bictegravir, Dolutegravir, Cabotegravir or their pharmaceutically acceptable salts.

Description of Related Art

Bictegravir developed by Gilead Sciences, is a potent HIV integrase inhibitor that causes a rapid reduction of HIV viral load in humans. It is chemically known as (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-][1,3]oxazepine-10-carboxamide and structurally represented as.

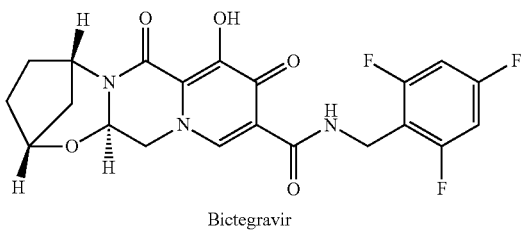

Bictegravir

PCT publications WO 2014/100323 A1, WO 2015/006731 A1, WO 2015/195656 A1, WO 2015/195656 A1 and WO 2018/229798 A1 describes processes for preparation of bictegravir intermediate or bictegravir or its pharmaceutically acceptable salts which are incorporated herein by reference.

Dolutegravir developed by ViiV Healthcare/GlaxoSmithKline for the treatment of human immunodeficiency virus (HIV)-1 infection. It is chemically known as (4R,12aS)-9-{[(2,4-difluorophenyl)methyl]carbamoyl}-4-methyl-6,8-dioxo-3,4,6,8,12,12a-hexahydro-2H-pyrido[1',2':4,5]pyrazino[2,1-b][1,3]oxazin-7-olate, and structurally represented as.

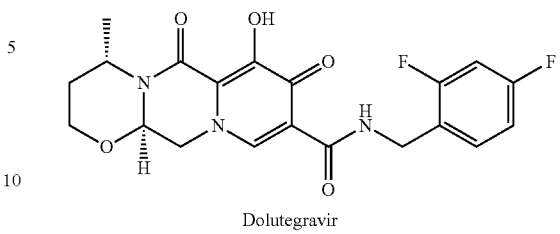

Dolutegravir

Cabotegravir is a human immunodeficiency virus type 1 (HIV-1) integrase strand transfer inhibitor (INSTI) currently under development for the treatment of HIV-1 infection in combination with other antiretroviral agents. It is chemically known as (3S,11aR)—N-[(2,4-Difluorophenyl)methyl]-2,3,5,7,11,11a-hexahydro-6-hydroxy-3-methyl-5,7-dioxooxazolo[3,2-a]pyrido[1,2-d]pyrazine-8-carboxamide, and structurally represented as.

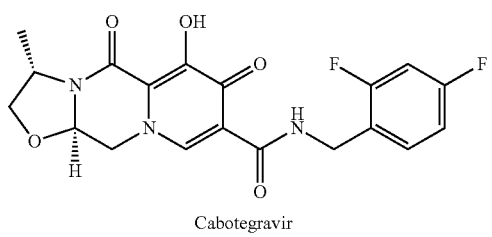

Cabotegravir

PCT publications WO 2006/116764 A1, WO 2010/068262 A1, WO 2010/068253 A1, WO 2012/018065 A1, WO 2014/128545 A1, WO 2015/019310 A1, WO 2015/111080 A1, WO 2015/110897 A1, WO 2016/092527 A1, WO 2016/113372 A1 describes processes for preparation of dolutegravir/cabotegravir intermediate or dolutegravir/cabotegravir or its pharmaceutically acceptable salts which are incorporated herein by reference.

The process of the present invention provides a process for the preparation of intermediate which is cost effective, having greater yields, easy to operate, and having high degree of chromatographic and optical purity.

SUMMARY OF THE INVENTION

The present invention provides a process for the preparation of the intermediate compound of formula (III) and intermediate compound of formula (iii).

The present invention further relates to converting intermediate compound of formula (III) and intermediate compound of formula (iii) obtained by the process of the present invention to HIV Integrase Inhibitor such as bictegravir of formula (I), dolutegravir of formula (I'), cabotegravir of formula (I") or their pharmaceutically acceptable salts.

DESCRIPTION OF THE INVENTION

The present invention relates to a process for preparation of compound of formula (III):

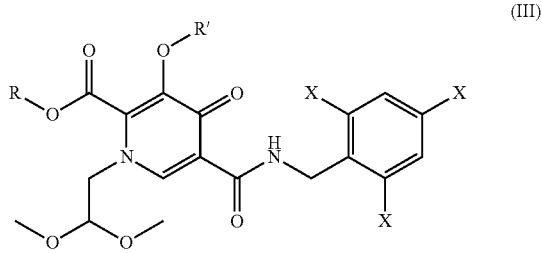

wherein, R is methyl or ethyl; R' is methyl or benzyl and X is hydrogen or fluorine; comprising reacting the compound of formula (II):

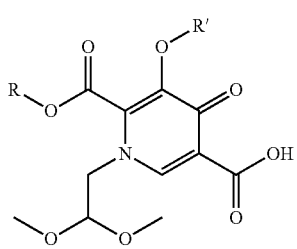

wherein, R and R' are as defined above;
with amine of formula (II'):

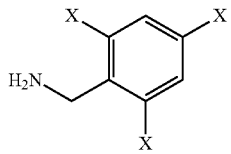

wherein, X is as defined above;
in presence of pivaloyl chloride and base.

The base used for the above reaction may be organic or inorganic. Organic base may be selected from but not limited to pyridine, dimethyl amine, triethyl amine, N,N-diisopropylethyl amine, 1,8-1,8-Diazabicyclo[5.4.0]undec-7-ene (DBU), N-methyl morpholine, N,N-dimethyl piperazine, or N-methyl piperidine. Inorganic base may be selected from but not limited to sodium hydroxide, potassium hydroxide, lithium hydroxide, ammonium hydroxide, sodium carbonate, potassium carbonate, sodium bicarbonate, potassium bicarbonate, sodium methoxide, potassium methoxide, potassium tert. butoxide, sodium acetate, or potassium acetate, and the like.

The above reaction is optionally carried out in a suitable solvent. Suitable solvent may be selected from but not limited to esters selected from ethyl acetate, isopropyl acetate; ethers selected from tetrahydrofuran, 2-methyl tetrahydrofuran, t-butyl methyl ether; alcohols selected from methanol, ethanol, isopropanol, t-butanol; ketones selected from acetone, methyl isobutyl ketone, methyl ethyl ketone; alkylnitriles selected from acetonitrile, propionitrile; hydrocarbons including halogenated hydrocarbons selected from toluene, xylene, dichloromethane or mixture thereof.

In another aspect, the invention provides process for preparation of HIV Integrase Inhibitor such as bictegravir (I) or dolutegravir (I') or cabotegravir (I") or their pharmaceutically acceptable salts comprising:

a) preparing the compound of formula (III):

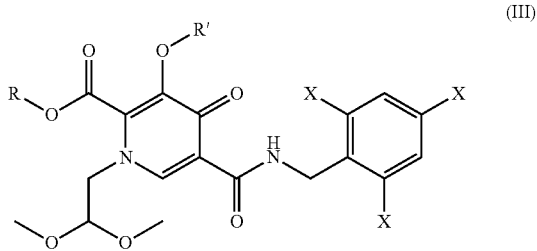

wherein, R is methyl or ethyl; R' is methyl or benzyl and X is hydrogen or fluorine; by reacting the compound of formula (II):

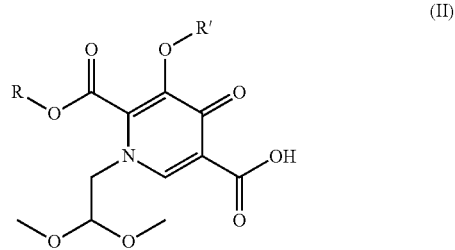

wherein, R and R' are as defined above;
with amine of formula (II'):

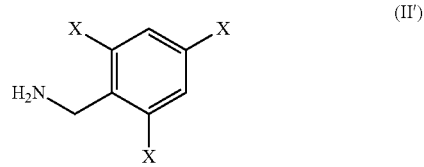

wherein, X is as defined above;
in presence of pivaloyl chloride and base;
b) converting the compound of formula (III) to bictegravir (I) or dolutegravir (I') or cabotegravir (I") or their pharmaceutically acceptable salts.

The base used in step a) of the above reaction may be inorganic or organic. Organic base may be selected from but not limited to pyridine, dimethyl amine, triethyl amine, N,N-diisopropylethyl amine, 1,8-1,8-Diazabicyclo[5.4.0] undec-7-ene (DBU), N-methyl morpholine, N,N-dimethyl piperazine or N-methyl piperidine. Inorganic base may be selected from but not limited to sodium hydroxide, potassium hydroxide, lithium hydroxide, ammonium hydroxide, sodium carbonate, potassium carbonate, sodium bicarbonate, potassium bicarbonate, sodium methoxide, potassium methoxide, potassium tert. butoxide, sodium acetate or potassium acetate, and the like. The step a) is optionally carried out in a suitable solvent. Suitable solvent may be selected from but not limited to esters selected from ethyl acetate, isopropyl acetate; ethers selected from tetrahydrofuran, 2-methyl tetrahydrofuran, t-butyl methyl ether; alcohols selected from methanol, ethanol, isopropanol, t-butanol; ketones selected from acetone, methyl isobutyl ketone, methyl ethyl ketone; alkylnitriles selected from acetonitrile, propionitrile; hydrocarbons including halogenated hydrocarbons selected from toluene, xylene, dichloromethane or mixture thereof.

In yet another aspect, the invention provides process for preparation of HIV Integrase Inhibitor such as bictegravir (I) or dolutegravir (I') or cabotegravir (I") or their pharmaceutically acceptable salts comprising:

a) preparing the compound of formula (III):

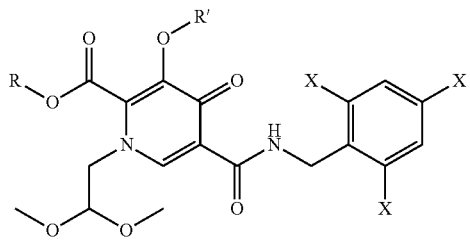
(III)

wherein, R is methyl or ethyl; R' is methyl or benzyl and X is hydrogen or fluorine;
by reacting the compound of formula (II):

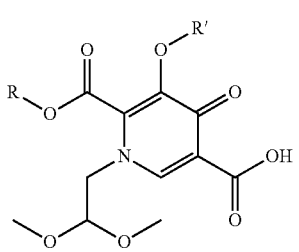
(II)

wherein, R and R' are as defined above;
with amine of formula (II'):

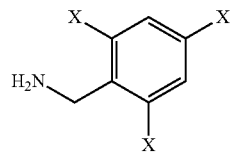
(II')

wherein, X is as defined above;
in presence of pivaloyl chloride and base;
b) reacting compound of formula (III) with acid to give compound of formula (IV):

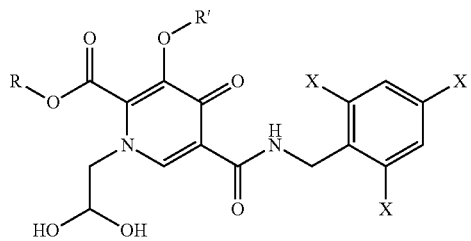
(IV)

wherein, R, R' and X are as defined above;
c) reacting compound of formula (IV) with (1R,3S)-3-aminocyclopentanol or its salt in presence of base to give compound of formula (V):

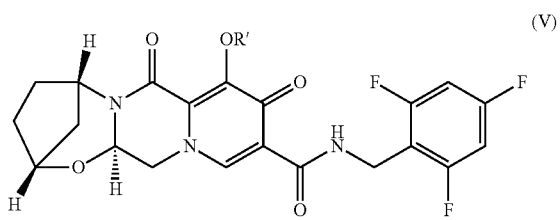
(V)

wherein, R' is as defined above;
or
reacting compound of formula (IV) with (R)-3-aminobutan-1-ol or its salt in presence of base to give compound of formula (V'):

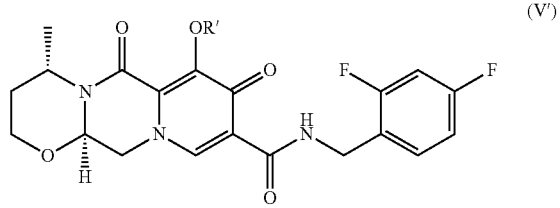
(V')

wherein, R' is as defined above;
or
reacting compound of formula (IV) with (2S)-2-amino-1-propanol or its salt in presence of base to give compound of formula (V"):

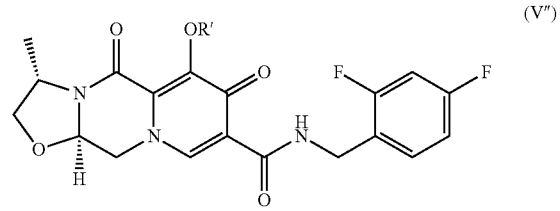
(V")

wherein, R' is as defined above;
d) deprotecting compound of formula (V) to give bictegravir (I):

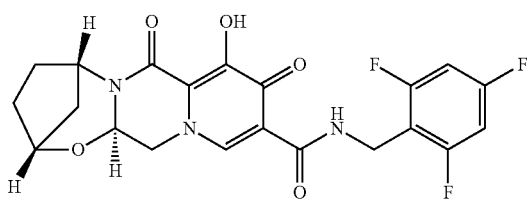

(I)

or
deprotecting compound of formula (V') to give dolutegravir (I'):

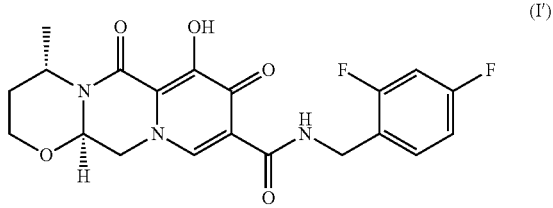 [SMILES: C[C@H]1CCO[C@@H]2Cn3cc(C(=O)NCc4ccc(F)cc4F)c(=O)c(O)c3C(=O)N12]

(I')

or
deprotecting compound of formula (V'') to give cabotegravir (I''):

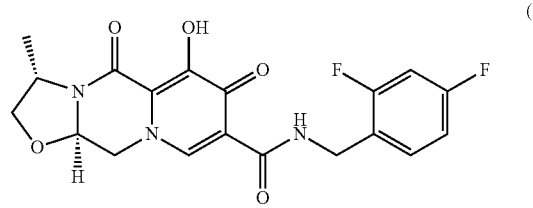

(I'')

e) optionally converting bictegravir (I) or dolutegravir (I') or cabotegravir (I'') to their pharmaceutically acceptable salts.

The base used in step a) and step c) of the above reaction may be organic or inorganic. Organic base may be selected from but not limited to pyridine, dimethyl amine, triethyl amine, N,N-diisopropylethyl amine, 1,8-1,8-Diazabicyclo[5.4.0]undec-7-ene (DBU), N-methyl morpholine, N,N-dimethyl piperazine or N-methyl piperidine. Inorganic base may be selected from but not limited to sodium hydroxide, potassium hydroxide, lithium hydroxide, ammonium hydroxide, sodium carbonate, potassium carbonate, sodium bicarbonate, potassium bicarbonate, sodium methoxide, potassium methoxide, potassium tert. butoxide, sodium acetate or potassium acetate, and the like.

The step a) is optionally carried out in a suitable solvent. Suitable solvent may be selected from but not limited to esters selected from ethyl acetate, isopropyl acetate; ethers selected from tetrahydrofuran, 2-methyl tetrahydrofuran, t-butyl methyl ether; alcohols selected from methanol, ethanol, isopropanol, t-butanol; ketones selected from acetone, methyl isobutyl ketone, methyl ethyl ketone; alkylnitriles selected from acetonitrile, propionitrile; hydrocarbons including halogenated hydrocarbons selected from toluene, xylene, dichloromethane or mixture thereof.

The acid used in step b) may be selected from but not limited to methanesulfonic acid, sulfuric acid, hydrochloric acid, trifluoroacetic acid, p-toluenesulfonic acid, acetic acid, formic acid, propionic acid, butyric acid or mixture thereof.

The step b) is optionally carried out in a suitable solvent. Suitable solvent may be selected from but not limited to acetonitrile, propionitrile, tetrahydroduran, 1,4-dioxane, ethyl acetate or a mixture thereof.

The amino alcohol used in step c) that is (1R,3S)-3-aminocyclopentanol for preparation of bictegravir, (R)-3-amino-butan-1-ol for preparation of dolutegravir and (2S)-2-amino-1-propanol for preparation of cabotegravir can be used in the form of its salt selected from but not limited to hydrochloric acid, acetic acid, methanesulfonic acid, and S-mandelic acid.

The step c) is optionally carried out in a suitable solvent. Suitable solvent may be selected from but not limited to acetonitrile, propionitrile, tetrahydroduran, ethyl acetate, toluene, 2-methyl tetrahydrofuran, isopropyl acetate, dichloromethane, or a mixture thereof.

Deprotecting involves the removal of R' group by suitable deprotection method known in the art depending upon the nature of protecting group. Suitable deprotection method may be selected from but not limited to hydrogenation or treatment with Lewis acid in a suitable solvent.

The deprotection by hydrogenation may be performed in the presence of a catalyst. The catalyst used may be selected from but not limited to platinum on carbon, palladium on carbon and the like; palladium hydroxide on carbon; platinum hydroxide on carbon; platinum oxide or raney nickel; more preferably palladium on carbon.

Lewis acid may be selected from group but not limited to lithium bromide, magnesium bromide, aluminium bromide, lithium chloride, magnesium chloride, aluminium chloride. More preferably metal salt used is lithium bromide.

The suitable solvent may be selected from but not limited to methanol, isopropanol, ethanol, acetone, methylene chloride, dimethyl sulfoxide, acetonitrile, tetrahydrofuran, dimethylformamide, dimethylacetamide, diisopropyl ether or mixture thereof.

Deprotection is carried out, when R' is benzyl by contacting the benzyl protected compound with hydrogen in presence of a catalyst and a suitable solvent. The catalyst used is preferably a transition metal catalyst, more preferably catalyst is a palladium.

Deprotection is carried out, when R' is methyl by contacting the methyl protected compound with Lewis acid in a suitable solvent. Lewis acid may be selected from group but not limited to lithium bromide, magnesium bromide, aluminium bromide, lithium chloride, magnesium chloride, aluminium chloride. More preferably metal salt used is lithium bromide.

Suitable solvent that can be used may be selected from but not limited to methanol, ethanol, isopropanol, acetone, methylene chloride, dimethyl sulfoxide, acetonitrile, tetrahydrofuran, dimethylformamide, dimethylacetamide, diisopropyl ether or mixture thereof.

In another aspect, the present invention relates to a process for preparation of compound of formula (iii):

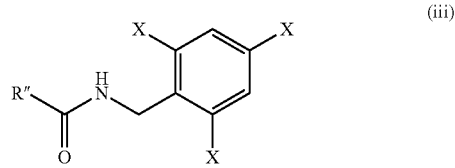

(iii)

wherein, R" is:

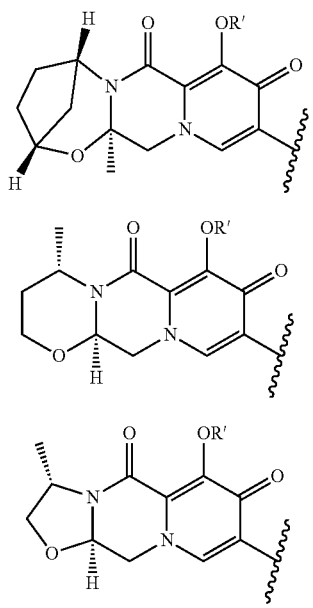

R' is methyl or benzyl and X is hydrogen or fluorine; comprising reacting the compound of formula (ii):

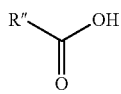

wherein, R" is as defined above;
with amine of formula (II'):

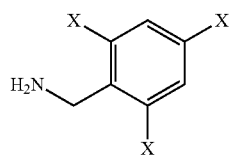

wherein, X is as defined above;
in presence of pivaloyl chloride and base.

The base used for the above reaction may be organic or inorganic. Organic base may be selected from but not limited to pyridine, dimethyl amine, triethyl amine, N,N-diisopropylethyl amine, 1,8-1,8-Diazabicyclo[5.4.0]undec-7-ene (DBU), N-methyl morpholine, N,N-dimethyl piperazine or N-methyl piperidine. Inorganic base may be selected from but not limited to sodium hydroxide, potassium hydroxide, lithium hydroxide, ammonium hydroxide, sodium carbonate, potassium carbonate, sodium bicarbonate, potassium bicarbonate, sodium methoxide, potassium methoxide, potassium tert. butoxide, sodium acetate or potassium acetate, and the like.

The above reaction is optionally carried out in a suitable solvent. Suitable solvent may be selected from but not limited to esters selected from ethyl acetate, isopropyl acetate; ethers selected from tetrahydrofuran, 2-methyl tetrahydrofuran, t-butyl methyl ether; alcohols selected from methanol, ethanol, isopropanol, t-butanol; ketones selected from acetone, methyl isobutyl ketone, methyl ethyl ketone; alkylnitriles selected from acetonitrile, propionitrile; hydrocarbons including halogenated hydrocarbons selected from toluene, xylene, dichloromethane or mixture thereof.

In another aspect, the invention provides process for preparation of HIV Integrase Inhibitor such as bictegravir (I) or dolutegravir (I') or cabotegravir (I") or their pharmaceutically acceptable salts comprising:

a) preparing the compound of formula (iii):

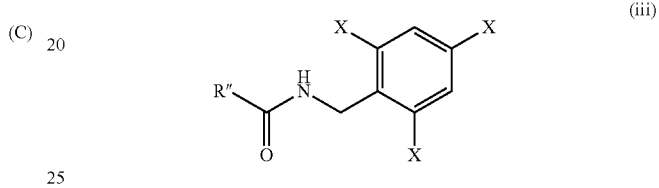

wherein, R" is:

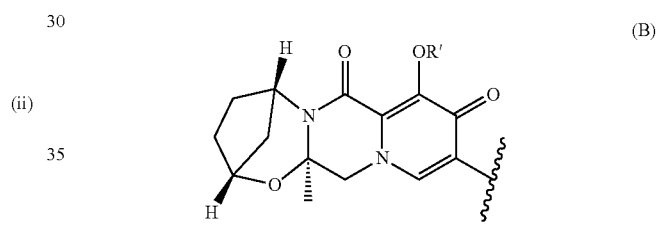

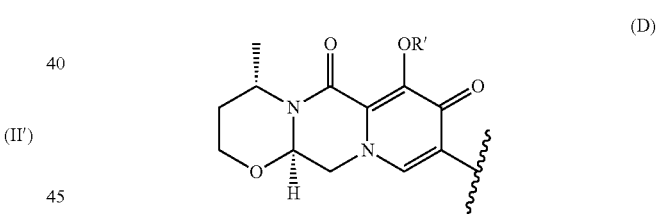

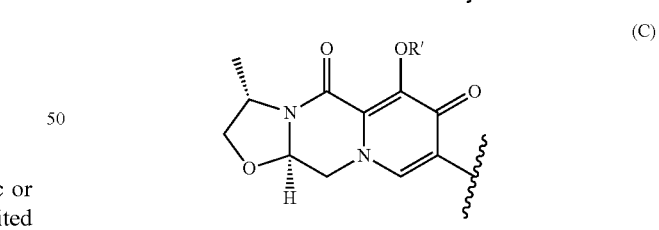

R' is methyl or benzyl and X is hydrogen or fluorine;
by reacting the compound of formula (ii):

wherein, R" is as defined above;
with amine of formula (II'):

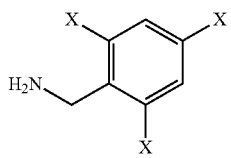

wherein, X is as defined above
in presence of pivaloyl chloride and base;
b) converting the compound of formula (iii) to bictegravir (I) or dolutegravir (I') or cabotegravir (I") or their pharmaceutically acceptable salts.

The base used in step a) of the above reaction may be inorganic or organic. Organic base may be selected from but not limited to pyridine, dimethyl amine, triethyl amine, N,N-diisopropylethyl amine, 1,8-1,8-Diazabicyclo[5.4.0]undec-7-ene (DBU), N-methyl morpholine, N,N-dimethyl piperazine or N-methyl piperidine. Inorganic base may be selected from but not limited to sodium hydroxide, potassium hydroxide, lithium hydroxide, ammonium hydroxide, sodium carbonate, potassium carbonate, sodium bicarbonate, potassium bicarbonate, sodium methoxide, potassium methoxide, potassium tert. butoxide, sodium acetate or potassium acetate, and the like.

The step a) is optionally carried out in a suitable solvent. Suitable solvent may be selected from but not limited to esters selected from ethyl acetate, isopropyl acetate; ethers selected from tetrahydrofuran, 2-methyl tetrahydrofuran, t-butyl methyl ether; alcohols selected from methanol, ethanol, isopropanol, t-butanol; ketones selected from acetone, methyl isobutyl ketone, methyl ethyl ketone; alkylnitriles selected from acetonitrile, propionitrile; hydrocarbons including halogenated hydrocarbons selected from toluene, xylene, dichloromethane or mixture thereof.

In yet another aspect, the invention provides process for preparation of HIV Integrase Inhibitor such as bictegravir (I) or dolutegravir (I') or cabotegravir (I") or their pharmaceutically acceptable salts comprising:
a) preparing the compound of formula (iii):

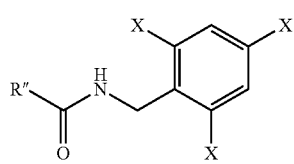

wherein, R" is:

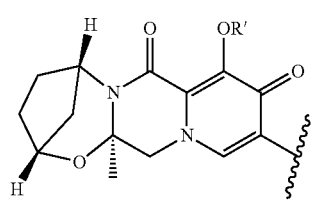

(B)

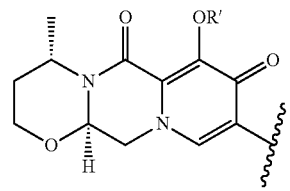

(D)

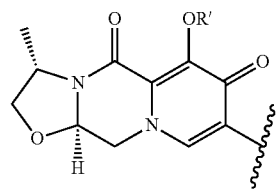

(C)

R' is methyl or benzyl and X is hydrogen or fluorine;
by reacting the compound of formula (ii):

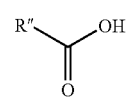

(ii)

wherein, R" is as defined above;
with amine of formula (II'):

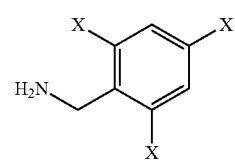

(II')

wherein, X is as defined above;
in presence of pivaloyl chloride and base;
b) deprotecting compound of formula (iii) to give bictegravir (I) or dolutegravir (I') or cabotegravir (I").
c) optionally converting bictegravir (I) or dolutegravir (I') or cabotegravir (I") to their pharmaceutically acceptable salts.

The base used in step a) of the above reaction may be organic or inorganic. Organic base may be selected from but not limited to pyridine, dimethyl amine, triethyl amine, N,N-diisopropylethyl amine, 1,8-1,8-Diazabicyclo[5.4.0]undec-7-ene (DBU), N-methyl morpholine, N,N-dimethyl piperazine or N-methyl piperidine. Inorganic base may be selected from but not limited to sodium hydroxide, potassium hydroxide, lithium hydroxide, ammonium hydroxide, sodium carbonate, potassium carbonate, sodium bicarbonate, potassium bicarbonate, sodium methoxide, potassium methoxide, potassium tert. butoxide, sodium acetate or potassium acetate, and the like.

The step a) is optionally carried out in a suitable solvent. Suitable solvent may be selected from but not limited to esters selected from ethyl acetate, isopropyl acetate; ethers selected from tetrahydrofuran, 2-methyl tetrahydrofuran, t-butyl methyl ether; alcohols selected from methanol, ethanol, isopropanol, t-butanol; ketones selected from acetone, methyl isobutyl ketone, methyl ethyl ketone; alkylnitriles selected from acetonitrile, propionitrile; hydrocarbons including halogenated hydrocarbons selected from toluene, xylene, dichloromethane or mixture thereof.

Deprotecting involves the removal of R' group by suitable deprotection method known in the art depending upon the nature of protecting group. Suitable deprotection method may be selected from but not limited to hydrogenation or treatment with Lewis acid in a suitable solvent.

The deprotection by hydrogenation may be performed in the presence of a catalyst. The catalyst used may be selected from but not limited to platinum on carbon, palladium on carbon and the like; palladium hydroxide on carbon; platinum hydroxide on carbon; platinum oxide or raney nickel; more preferably palladium on carbon.

Lewis acid may be selected from group but not limited to lithium bromide, magnesium bromide, aluminium bromide, lithium chloride, magnesium chloride, aluminium chloride. More preferably metal salt used is lithium bromide.

The suitable solvent may be selected from but not limited to methanol, isopropanol, ethanol, acetone, methylene chloride, dimethyl sulfoxide, acetonitrile, tetrahydrofuran, dimethylformamide, dimethylacetamide, diisopropyl ether or mixture thereof.

Deprotection is carried out, when R' is benzyl by contacting the benzyl protected compound with hydrogen in presence of a catalyst and a solvent. The catalyst used is preferably a transition metal catalyst, more preferably catalyst is a palladium.

Deprotection is carried out, when R' is methyl by contacting the methyl protected compound with Lewis acid in a suitable solvent. Lewis acid may be selected from group but not limited to lithium bromide, magnesium bromide, aluminium bromide, lithium chloride, magnesium chloride, aluminium chloride. More preferably metal salt used is lithium bromide.

Suitable solvent that can be used may be selected from but not limited to methanol, ethanol, isopropanol, acetone, methylene chloride, dimethyl sulfoxide, acetonitrile, tetrahydrofuran, dimethylformamide, dimethylacetamide, diisopropyl ether or mixture thereof.

The compound of the formula (II) and compound of the formula (ii) used herein for the process of the present invention can be obtained by the processes known in the art, for example as described in WO 2011/129095 A1, WO 2011/119566 A1, WO 2012/018065 A1, WO 2014/100323 A1 which are incorporated herein by reference.

The intermediate compound of the formula (III) and intermediate compound of the formula (iii) obtained by the process of the present invention can also be converted to bictegravir (I), dolutegravir (I'), and cabotegravir (I") or their pharmaceutically acceptable salts by the processes known in the art.

HIV Integrase Inhibitor such as bictegravir (I), dolutegravir (I'), and cabotegravir (I") obtained by the process of the present invention are optionally converted to their pharmaceutically acceptable salts. The pharmaceutically acceptable salt may be sodium, potassium, calcium, lithium, magnesium. More preferably pharmaceutically acceptable salt is sodium salt.

Pharmaceutically acceptable salt may be prepared by reacting respective HIV Integrase Inhibitor with suitable alkali metal hydroxide in a suitable solvent. Suitable alkali metal hydroxide are selected from but not limited to sodium hydroxide, potassium hydroxide, calcium hydroxide, lithium hydroxide, magnesium hydroxide. More preferably alkali metal hydroxide is sodium hydroxide. Suitable solvent that can be used may be selected from but not limited to alcohols selected from methanol, ethanol, isopropanol, t-butanol; ketones selected from acetone, methyl isobutyl ketone, methyl ethyl ketone; esters selected from ethyl acetate, isopropyl acetate or mixture thereof.

HIV Integrase Inhibitor such as bictegravir, dolutegravir, and cabotegravir or their pharmaceutically acceptable salts obtained by the process of the present invention are optionally purified from solvent selected from acetone, methanol, ethanol, dichloromethane, chloroform, 1,2-dichloroethane, carbon tetrachloride, ethyl acetate, methyl acetate, isobutyl acetate, water or mixture thereof.

HIV Integrase Inhibitor such as bictegravir, dolutegravir, and cabotegravir or their pharmaceutically acceptable salts obtained by the process of the present invention are having a purity of greater than about 95%, or greater than about 98%, or greater than about 99%, or greater than about 99.5%, or greater than about 99.9%, as determined using high performance liquid chromatography (HPLC).

The example provided herein are for the purpose of illustration only and are not to be construed as limiting the scope of the invention in any way.

EXAMPLES

Example 1: Preparation of Methyl 1-(2,2-dimethoxyethyl)-3-methoxy-4-Oxo-5-((2,4,6-trifluorobenzyl) carbamoyl)-1,4-dihydropyridine-2-carboxylate [III: R and R'=Methyl, X=Fluorine]

57.78 gm triethyl amine was added to 150 gm of compound of formula (II: R and R'=Methyl) in 750 ml dichloromethane, reaction mixture was then cooled to 0-5° C. followed by addition of 68.5 gm pivaloyl chloride at 0-10° C. To this was then added 88 gm 2,4,6-Trifluorobenzylamine at 0-10° C. and the stirred for 2-2.5 hours at 0-30° C. To this 750 ml of 10% HCl solution was added, organic layer separated and was washed with sodium bicarbonate solution. The organic layer was concentrated and then charged 750 ml isopropanol and 750 ml dichloromethane, heated to 35-40° C., stirred and maintained at 35-40° C. for 1 hour, filtered, washed with isopropanol and solid obtained was dried to give 203 gm Methyl 1-(2,2-dimethoxyethyl)-3-methoxy-4-oxo-5-((2,4,6-trifluorobenzyl) carbamoyl)-1,4-dihydropyridine-2-carboxylate.

Yield: 93.12%.

HPLC Purity: 98%.

Example 2: Preparation of Methyl 1-(2,2-dihydroxyethyl)-3-methoxy-4-oxo-5-((2,4,6-trifluorobenzyl) carbamoyl)-1,4-dihydro pyridine-2-carboxylate [IV: R and R'=Methyl, X=Fluorine]

189 gm of acetic acid and 7.54 gm of methane sulfonic acid was added to 180 gm of compound of formula (III: R and R'=Methyl, X=Fluorine) in 900 ml acetonitrile. The reaction mixture was heated to 80-85° C. and stirred for 6-8 hours at 60-70° C. The reaction was cooled to 20-30° C. and 900 ml water was added. The mixture was then concentrated to remove acetonitrile. The resultant slurry was then maintained at 20-30° C. for 2-2.5 hours, filtered, washed with water (500 ml) and dried to give 150 gm Methyl 1-(2,2- dihydroxyethyl)-3-methoxy-4-oxo-5-((2,4,6-trifluorobenzyl) carbamoyl)-1,4-dihydro pyridine-2-carboxylate.
Yield: 88.75%.
HPLC Purity: 95%.

Example 3: Preparation of (2R,5S,13aR)-8-methoxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide [iii: R''=B, R'=Methyl and X=Fluorine]

50 g compound of formula (ii: R''=B) was charged along with 500 mL of dichloromethane followed by 19 g of triethylamine base and stirred for 30-60 minutes at 20-30° C. The reaction mass was cooled to 0-10° C., added pivaloyl chloride 21.6 g and stirred for 30-60 minutes at 0-10° C., then addition of 25.2 g 2,4,6-trifluoro benzyl amine followed by stirring for 30-60 minutes at 10-20° C.

Washed the organic layer with 250 mL 5% aq. Sodium bicarbonate solution followed by 250 mL water wash then concentrated the reaction mass. The reaction mass was cooled to 20-30° C., charged 100 mL isopropyl alcohol, stirred for 30-60 minutes, again cooled to 0-10° C. and stirred, filtered, washed with isopropyl alcohol and dried to give 60 g compound of formula (iii).
Yield: 85%.
HPLC Purity: 96%.

Example 4: Preparation of Bictegravir (I)

57.06 gm of potassium acetate and 31.99 gm (1R, 3S)-3-aminocyclopentanol HCl was added to 100 gm of compound of formula (IV: R and R'=Methyl, X=Fluorine) in 500 ml dichloromethane. The reaction was heated to 40-50° C. and maintained for 6-8 hours. 400 ml water was then charged to reaction, separated layers, washed organic layer which contains compound of formula (V) with 10% brine solution (400 ml).

400 ml acetonitrile and 50 gm lithium bromide was added to above organic layer, heated the reaction to 40-50° C. and maintained for 2-4 hours. 5% aq. HCl was added to the reaction, separated the layers, reaction was concentrated to remove dichloromethane and then added 400 ml methanol. The reaction was cooled to 20-30° C., filtered, washed with methanol and dried to give 67.5 gm bictegravir.
Yield: 64.63%.
HPLC Purity: 97%.

Example 5: Purification of Bictegravir (I)

65 gm bictegravir in 130 ml methanol was heated to 60-70° C. 30-60 minutes, cooled, filtered, washed with methanol and dried under vacuum to give pure 50 gm bictegravir.
Yield: 76.92%.
HPLC Purity: 99%.

Example 6: Purification of Bictegravir (I)

50 gm of bictegravir in 500 ml methanol and 100 ml DCM was stirred for 1 hour, filtered the reaction. Dichloromethane was then removed by distillation from filtrate, reaction heated to 60-70° C., stirred and maintained for 1-1.5 hours, cooled to 0-10° C., filtered, washed methanol and dried to give 45 gm bictegravir.
Yield: 90%.
HPLC Purity: 99%.

Example 7: Preparation of Bictegravir Sodium (I)

50 gm of bictegravir in 250 ml dichloromethane and 500 ml ethanol with 2.5 gm activated charcoal was heated to 40° C., filtered the reaction. Dichloromethane was then removed by distillation, reaction heated to 60-70° C. for 30 minutes. NaOH solution (4.45 gm NaOH in 111 ml water) was then added to reaction, heated reaction to 70-80° C., stirred and maintained for 1-1.5 hours, cooled to 20-30° C., filtered, washed with ethanol and dried to give 45 gm bictegravir sodium.
Yield: 85.79%.
HPLC Purity: 99%.

Example 8: Preparation of Bictegravir (I)

29 gm triethyl amine was added to 60 gm of compound of formula (ii: R''=B) in 300 ml dichloromethane, reaction mixture was then cooled to 0-5° C. followed by addition of 32 gm pivaloyl chloride at 0-10° C. To this was then added 30.2 gm 2,4,6-trifluorobenzylamine at 10-20° C. and the stirred for 1-1.5 hours at 20-30° C. To this was then added 300 ml 10% sodium bicarbonate solution, stirred and separated the organic layer.

240 ml acetonitrile was added to above organic layer, followed by addition of 32 gm lithium bromide. The reaction mixture was then heated to 40-50° C., stirred and maintained for 7-8 hrs. The reaction mixture was then cooled to 25-30° C. and then added 300 ml 5% aq. hydrochloric acid solution. Organic layer was separated, distilled and then charged with 120 ml methanol, heated, cooled, filtered, washed with methanol and dried to give 65 gm Bictegravir (I).
Yield: 77.20%.
HPLC Purity: 97%.

Example 9: Preparation of (3S,11aR)—N-(2,4-Difluorobenzyl)-6-methoxy-3-methyl-5,7-dioxo-2,3,5,7,11,11a-hexahydrooxazolo[3,2-a]pyrido[1,2-d]pyrazine-8-carboxamide [iii: R'=Methyl, X=F at $2^{nd}$ & $4^{th}$ Position and H at $6^{th}$ Position]

19 gm triethyl amine was added to 50 gm of compound of formula (ii: R''=C) in 400 ml dichloromethane, reaction mixture was then cooled to 0-5° C. followed by addition of 22.44 gm pivaloyl chloride at 0-10° C. To this was then added 26.74 gm 2,4-difluorobenzylamine at 0-10° C. and the stirred for 2-2.5 hours at 0-30° C. To this 250 ml of 10% HCl solution was added, organic layer separated and was washed with sodium bicarbonate solution. The organic layer was concentrated and then charged 250 ml isopropanol, reaction mass cooled to 0-10° C., stirred and maintained at 0-10° C. for 1-1.5 hr hour, filtered, washed with isopropanol and solid obtained was dried to give 47 gm (3S,11aR)—N-(2,4-difluorobenzyl)-6-methoxy-3-methyl-5,7-dioxo-2,3,5,7,11,11a-hexahydrooxazolo[3,2-a]pyrido[1,2-d]pyrazine-8-carboxamide.
Yield: 67%.
HPLC Purity: 96%.

Example 10: Preparation of Cabotegravir (I'')

20 gm lithium bromide was added to 40 gm of compound of formula (iii, R''=C & X=F at $2^{nd}$ & $4^{th}$ position and H at 6th position) in 400 ml acetonitrile, reaction mixture was then heated to 60-80° C., maintained for 6-7 hrs and then cooled to 20-30° C. To this was then added 40 ml 10% aq. HCl and 300 ml water. The solid obtained was filtered, washed with water and dried to give 36.5 gm Cabotegravir.

Yield: 94.41%.

HPLC Purity: 96%.

Example 11: Preparation of Cabotegravir Sodium (I")

35 gm of cabotegravir in 350 ml ethanol was heated to 70-80° C. To this was then added NaOH solution (3.8 gm NaOH in 92 ml water), heated reaction to 70-80° C., stirred and maintained for 1-1.5 hours, cooled to 20-30° C., maintained for 2-2.5 hours, filtered, washed with ethanol and dried to give 35 gm cabotegravir sodium.

Yield: 95%.

HPLC Purity: 97%.

We claim:

1. A process for preparation of the compound of formula (iii):

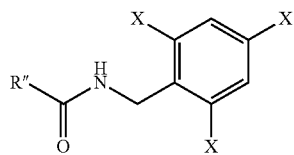

wherein, X is hydrogen or fluorine; R" is:

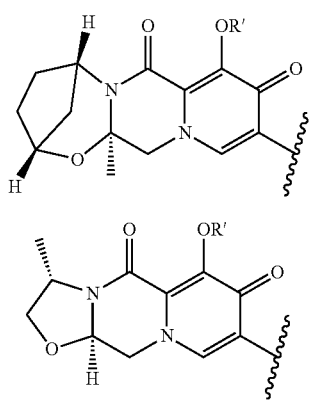

and R' is methyl or benzyl;
comprising reacting the compound of formula (ii):

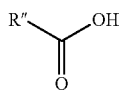

wherein, R" is as defined above;
with the amine of formula (II'):

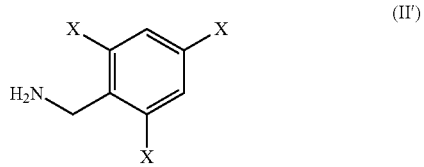

wherein, X is as defined above;
in the presence of pivaloyl chloride and base.

2. The process according to claim 1, wherein the base is organic or inorganic.

3. The process according to claim 2, wherein the organic base is selected from pyridine, dimethyl amine, triethyl amine, N,N-diisopropylethyl amine, 1,8-Diazabicyclo[5.4.0]undec-7-ene, N-methyl morpholine, N,N-dimethyl piperazine, or N-methyl piperidine.

4. The process according to claim 2, wherein the inorganic base is selected from sodium hydroxide, potassium hydroxide, lithium hydroxide, ammonium hydroxide, sodium carbonate, potassium carbonate, sodium bicarbonate, potassium bicarbonate, sodium methoxide, potassium methoxide, potassium tert-butoxide, sodium acetate, and potassium acetate.

5. The process according to claim 1, wherein the reaction is optionally carried out in a solvent selected from ester, ether, alcohol, ketone, alkyl nitriles, hydrocarbons, and mixtures thereof.

6. A process for preparation of bictegravir (I), cabotegravir (I"), or their pharmaceutically acceptable salts comprising:
preparing the compound of formula (iii):

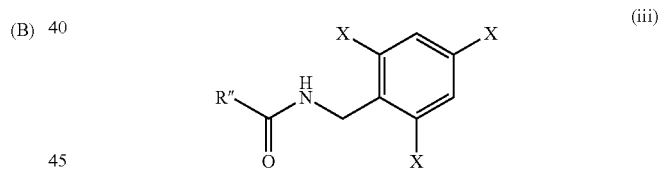

wherein, X is hydrogen or fluorine; R" is:

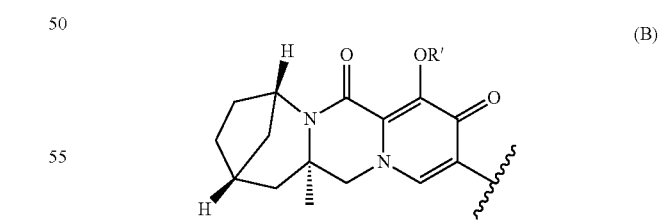

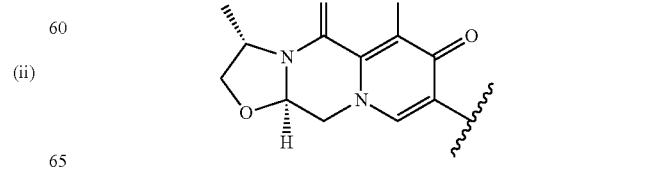

and R' is methyl or benzyl;
by reacting the compound of formula (ii):

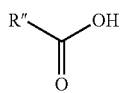

wherein, R" is as defined above;
with the amine of formula (II'):

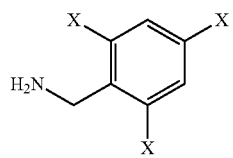

wherein, X is as defined above;
in the presence of pivaloyl chloride and base;
deprotecting the compound of formula (iii) by hydrogenation or treatment with a Lewis acid to give bictegravir (I), dolutegravir (I'), or cabotegravir (I"); and
optionally converting bictegravir (I), dolutegravir (I'), or cabotegravir (I") to their respective pharmaceutically acceptable salts.

7. The process according to claim 6, wherein the base is organic or inorganic.

8. The process according to claim 7, wherein the organic base is selected from pyridine, dimethyl amine, triethyl amine, N,N-diisopropylethyl amine, 1,8-Diazabicyclo [5.4.0]undec-7-ene, N-methyl morpholine, N,N-dimethyl piperazine, and N-methyl piperidine.

9. The process according to claim 7, wherein the inorganic base is selected from sodium hydroxide, potassium hydroxide, lithium hydroxide, ammonium hydroxide, sodium carbonate, potassium carbonate, sodium bicarbonate, potassium bicarbonate, sodium methoxide, potassium methoxide, potassium tert-butoxide, sodium acetate, and potassium acetate.

10. The process according to claim 6, wherein the reaction is carried out in a solvent selected from ester, ether, alcohol, ketone, alkyl nitriles, hydrocarbons, and mixtures thereof.

11. The process according to claim 6, wherein the Lewis acid is selected from the group consisting of lithium bromide, magnesium bromide, aluminum bromide, lithium chloride, magnesium chloride, and aluminum chloride.

12. A process for preparation of bictegravir (I), dolutegravir (I'), cabotegravir (I"), or their pharmaceutically acceptable salts comprising:
preparing the compound of formula (III):

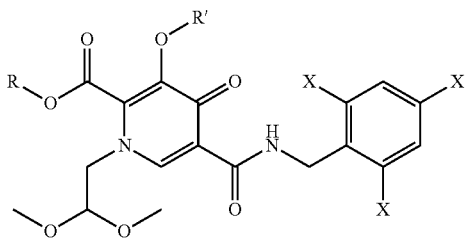

wherein, R is methyl or ethyl; R' is methyl or benzyl; and X is hydrogen or fluorine;
by reacting the compound of formula (II):

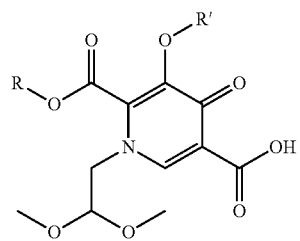

wherein, R and R' are as defined above;
with the amine of formula (II'):

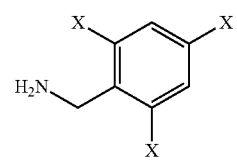

wherein, X is as defined above;
in presence of pivaloyl chloride and base;
reacting the compound of formula (III) with acid to give the compound of formula (IV):

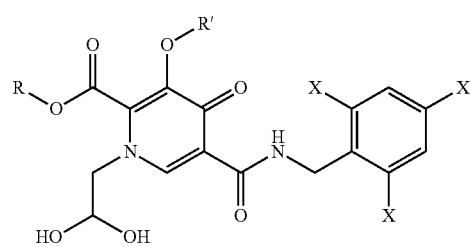

wherein, R, R' and X are as defined above;
reacting the compound of formula (IV) with (1R,3S)-3-aminocyclopentanol or its salt in presence of base to give the compound of formula (V):

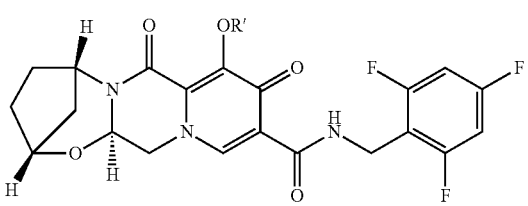

wherein, R' is as defined above;
or
reacting the compound of formula (IV) with (R)-3-aminobutan-1-ol or its salt in presence of base to give the compound of formula (V'):

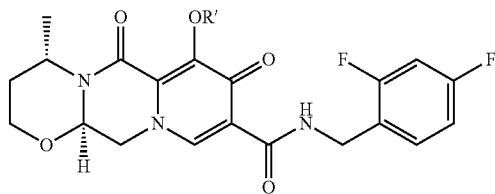

wherein, R' is as defined above;
or
reacting the compound of formula (IV) with (2S)-2-amino-1-propanol or its salt in presence of base to give the compound of formula (V"):

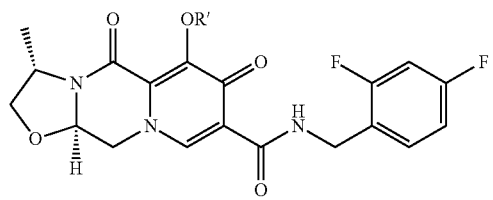

wherein, R' is as defined above;
deprotecting the compound of formula (V) to give bictegravir (I):

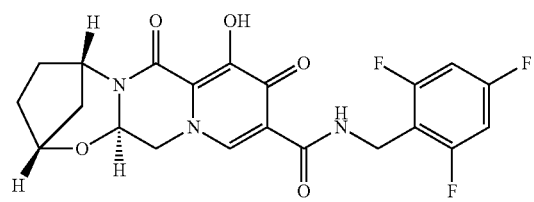

or
deprotecting the compound of formula (V') to give dolutegravir (I'):

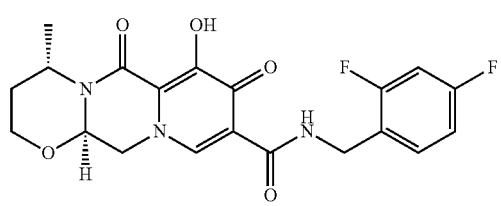

or
deprotecting the compound of formula (V") to give cabotegravir (I"):

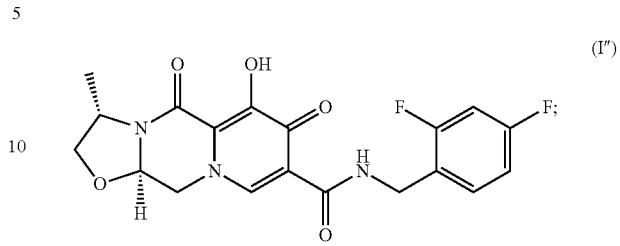

and optionally converting bictegravir (I), dolutegravir (I'), or cabotegravir (I") to their respective pharmaceutically acceptable salts.

13. The process according to claim 12, wherein the base is organic or inorganic.

14. The process according claim 13, wherein the organic base is selected from pyridine, dimethyl amine, triethyl amine, N,N-diisopropylethyl amine, 1,8-Diazabicyclo [5.4.0]undec-7-ene, N-methyl morpholine, N,N-dimethyl piperazine, or N-methyl piperidine.

15. The process according claim 13, wherein the inorganic base is selected from sodium hydroxide, potassium hydroxide, lithium hydroxide, ammonium hydroxide, sodium carbonate, potassium carbonate, sodium bicarbonate, potassium bicarbonate, sodium methoxide, potassium methoxide, potassium tert-butoxide, sodium acetate, and potassium acetate.

16. The process according to claim 12, wherein step a) is carried out in a solvent selected from ester, ether, alcohol, ketone, alkyl nitriles, hydrocarbons, and mixtures thereof.

17. The process according to claim 12, wherein the acid is selected from methanesulfonic acid, sulfuric acid, hydrochloric acid, trifluoroacetic acid, p-toluenesulfonic acid, acetic acid, formic acid, propionic acid, butyric acid, and mixtures thereof.

18. The process according to claim 12, wherein step b) is carried out in a solvent selected from acetonitrile, propionitrile, tetrahydroduran, 1,4-dioxane, ethyl acetate, and mixtures thereof.

19. The process according to claim 12, wherein step c) is carried out in a solvent selected from acetonitrile, propionitrile, tetrahydroduran, ethyl acetate, toluene, 2-methyl tetrahydrofuran, isopropyl acetate, dichloromethane, and mixtures thereof.

20. The process according to claim 12, wherein deprotection is carried out by hydrogenation or treatment with a Lewis acid.

* * * * *

UNITED STATES PATENT AND TRADEMARK OFFICE
CERTIFICATE OF CORRECTION

PATENT NO. : 11,248,005 B2  
APPLICATION NO. : 16/922260  
DATED : February 15, 2022  
INVENTOR(S) : Harishchandra Sambhaji Jadhav et al.

Page 1 of 1

It is certified that error appears in the above-identified patent and that said Letters Patent is hereby corrected as shown below:

In the Claims

Column 18, Lines 50-58, Claim 6, delete " " and insert -- --  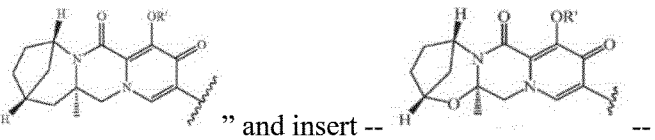

Column 19, Line 26, Claim 6, delete "(I), dolutegravir (I')," and insert -- (I) --

Column 19, Line 27, Claim 6, delete "(I), dolutegravir (I')," and insert -- (I) --

Column 22, Line 22, Claim 14, delete "according" and insert -- according to --

Column 22, Line 28, Claim 15, delete "according" and insert -- according to --

Column 22, Line 46, Claim 18, delete "tetrahydroduran," and insert -- tetrahydrofuran, --

Column 22, Line 50, Claim 19, delete "tetrahydroduran," and insert -- tetrahydrofuran, --

Signed and Sealed this  
Seventeenth Day of May, 2022

Katherine Kelly Vidal  
*Director of the United States Patent and Trademark Office*